(12) United States Patent
Aung et al.

(10) Patent No.: US 10,993,630 B2
(45) Date of Patent: May 4, 2021

(54) RESPIRATION RATE ESTIMATION FROM A PHOTOPLETHYSMOGRAPHY SIGNAL

(71) Applicant: Hill-Rom Services PTE. LTD., Singapore (SG)

(72) Inventors: Aye Aung, Singapore (SG); Yue Wang, Columbus, IN (US); Chau C. Ye, Singapore (SG); Suresha Venkataraya, Singapore (SG)

(73) Assignee: Hill-Rom Services PTE. LTD., Singapore (SG)

( * ) Notice: Subject to any disclaimer, the term of this patent is extended or adjusted under 35 U.S.C. 154(b) by 297 days.

(21) Appl. No.: 16/155,170

(22) Filed: Oct. 9, 2018

(65) Prior Publication Data
US 2019/0117097 A1    Apr. 25, 2019

Related U.S. Application Data

(60) Provisional application No. 62/574,322, filed on Oct. 19, 2017.

(51) Int. Cl.
*A61B 5/024*    (2006.01)
*A61B 5/0205*   (2006.01)
(Continued)

(52) U.S. Cl.
CPC ........ *A61B 5/02416* (2013.01); *A61B 5/0205* (2013.01); *A61B 5/02405* (2013.01);
(Continued)

(58) Field of Classification Search
CPC . A61B 5/02416; A61B 5/4836; A61B 5/7203; A61B 5/02405; A61B 5/7278; A61B 5/0205; A61B 5/0816; A61B 5/02
See application file for complete search history.

(56) References Cited

U.S. PATENT DOCUMENTS 6,709,402 B2   3/2004   Dekker
8,444,570 B2   5/2013   McGonigle et al.
(Continued)

FOREIGN PATENT DOCUMENTS

EP    3087915 A1    11/2016
WO    2017096428 A1    6/2017

OTHER PUBLICATIONS

J N A Mockridge, et. al., "Computerised determination of spontaneous inspiratory and expiratory times in premature neonates during intermittent positive pressure ventilation. I: a new technique", 1994, Archives of Disease in Childhood, (Year: 1994).*
(Continued)

*Primary Examiner* — Eric F Winakur
*Assistant Examiner* — Abid A Mustansir
(74) *Attorney, Agent, or Firm* — Barnes & Thornburg LLP

(57) ABSTRACT

A method of determining respiratory rate from a photoplethysmograph signal includes filtering the photoplethysmograph signal to create a filtered photoplethysmograph signal. The method also includes detecting peaks and valleys in the filtered photoplethysmograph signal to extract predetermined features from the filtered photoplethysmograph signal. The method also includes obtaining variation waveforms from the predetermined features. The method also includes removing outliers from each of variation waveforms. The method also includes interpolating for the outliers removed from each of the variation waveforms to acquire a frequency estimation of each of the variation waveforms. The method also includes determining a respiratory rate based on the frequency estimation of each of the variation waveforms. The method also includes determining a weighted average of the respiratory rate the variation waveforms to determine an estimated respiratory rate.

17 Claims, 14 Drawing Sheets

(51) Int. Cl.
*A61B 5/08* (2006.01)
*A61B 5/00* (2006.01)

(52) U.S. Cl.
CPC .......... *A61B 5/0816* (2013.01); *A61B 5/4836* (2013.01); *A61B 5/7203* (2013.01); *A61B 5/7278* (2013.01)

(56) References Cited

U.S. PATENT DOCUMENTS

| | | | |
|---|---|---|---|
| 8,801,620 B2 | 8/2014 | Melker et al. | |
| 8,882,676 B2 | 11/2014 | Hughes | |
| 10,004,427 B1* | 6/2018 | Shoeb | A61B 5/7221 |
| 2004/0267477 A1* | 12/2004 | Scott | G01R 31/31707 |
| | | | 702/108 |
| 2008/0262326 A1 | 10/2008 | Hete et al. | |
| 2009/0240126 A1 | 9/2009 | Baker, Jr. et al. | |
| 2010/0016694 A1* | 1/2010 | Martin | A61M 16/0051 |
| | | | 600/324 |
| 2011/0041849 A1* | 2/2011 | Chen | A61M 16/0057 |
| | | | 128/204.23 |
| 2011/0257489 A1* | 10/2011 | Banet | A61B 5/0809 |
| | | | 600/301 |
| 2012/0253156 A1* | 10/2012 | Muhlsteff | A61B 5/1116 |
| | | | 600/324 |
| 2015/0208964 A1 | 7/2015 | Addison et al. | |
| 2016/0134985 A1* | 5/2016 | Hashimoto | H04R 3/04 |
| | | | 704/503 |
| 2016/0345862 A1 | 12/2016 | Li | |

OTHER PUBLICATIONS

Medgadget, Nellcor Respiration Rate Monitoring Using a Pulse Oximeter Finger Sensor, Jun. 6, 2014, https://www.medgadget.com/2014/06/nellcor-respiration-rate-monitoring-using-a-pulse-oximeter-finger-sensor.html, 3 pages.

P. Leonard et al., "Standard Pulse Oximeters Can Be Used to Monitor Respiratory Rate", Emergency Medicine Journal, vol. 20(6): 524-525, Nov. 2003, https://www.ncbi.nlm.nih.gov/pmc/articles/PMC1726217/, 2 pages.

Paul S. Addison et al., "Pulse Oximetry-Derived Respiratory Rate in General Care Floor Patients", Journal of Clinical Monitoring and Computing, vol. 29, Issue 1, pp. 113-120, Feb. 2015, https://www.ncbi.nlm.nih.gov/pmc/articles/PMC1726217/, 8 pages.

Ainara Garde et al., "Estimating Respiratory and Heart Rates from the Correntropy Spectral Density of the Photoplethysmogram", Plos One, vol. 9, Issue 1, Jan. 2014, https://journals.plos.org/plosone/article?id=10.1371/journal.pone.0086427, 11 pages.

Walter Karlen et al., "Multiparameter Respiratory Rate Estimation from the Photoplethysmogram", IEEE Transactions on Biomedical Engineering, vol. 60, No. 7, pp. 1946-1953, Jul. 2013, http://www.capnobase.org/uploads/media/Karlen_et_al._-_2013_-_Multiparameter_respiratory_rate_estimation.pdf, 8 pages.

John Allen, "Photoplethysmography and its application in clinical physiological measurement", IOP Publishing, pp. R1-R39, Feb. 2007, http://iopscience.iop.org/article/10.1088/0967-3334/28/3/R01/meta; sessionid=27315E4A606987DE4B247938CA94313D.A.iopscience.cld.iop.org, 39 pages.

European Search Report, Application No. 181999715, dated Mar. 15, 2019, 5 pages.

* cited by examiner

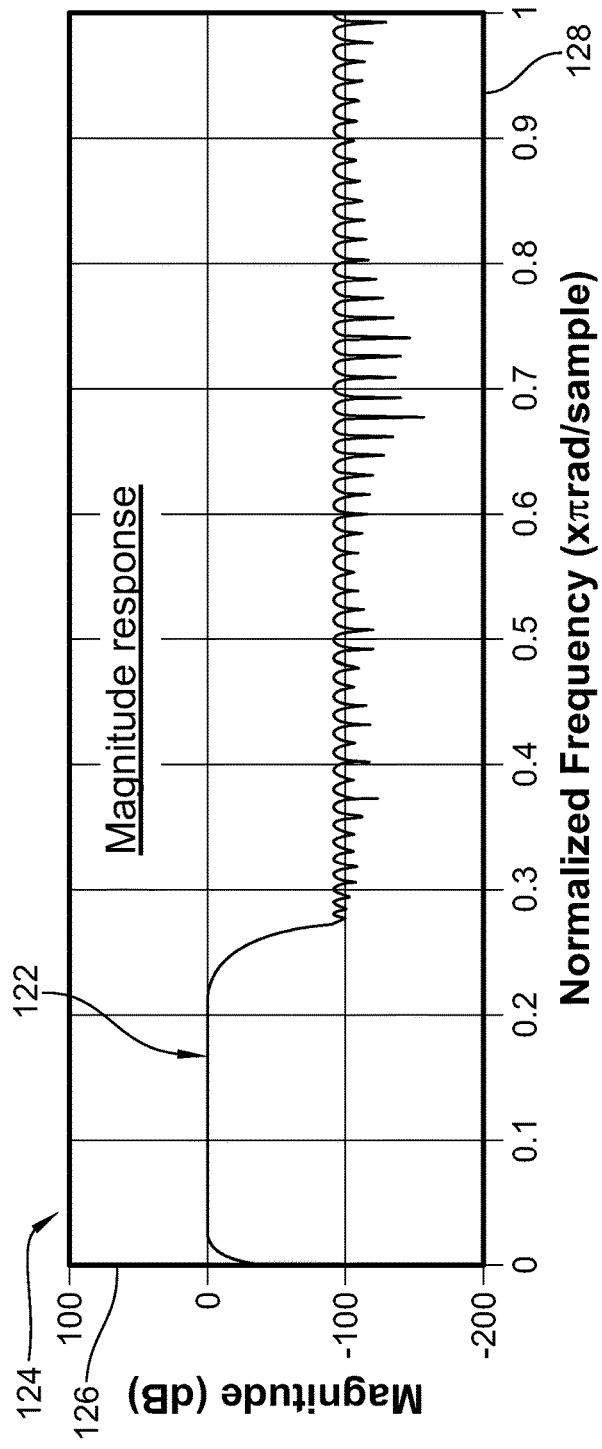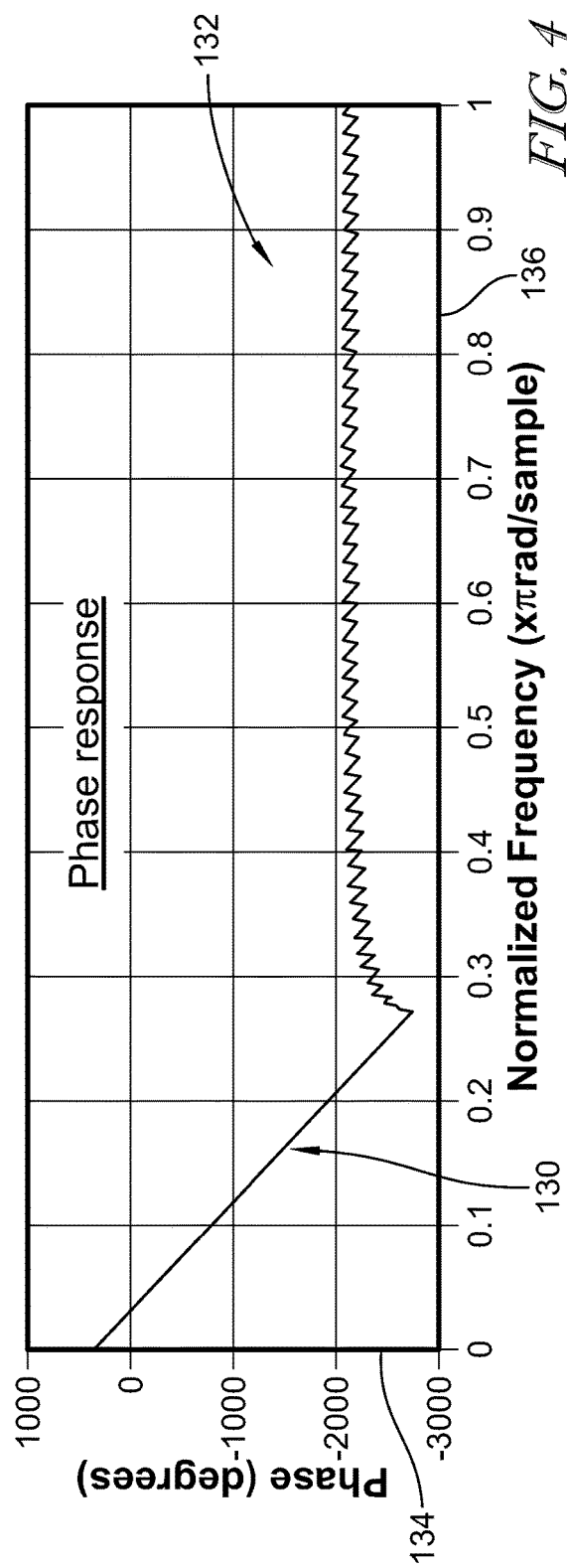
FIG. 4

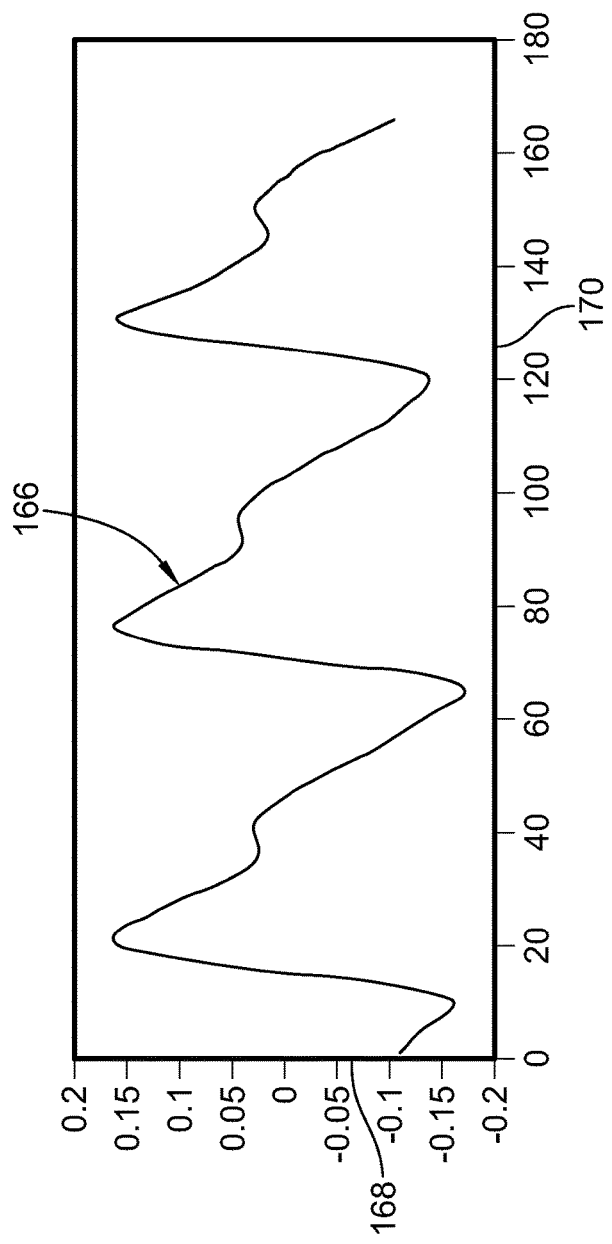
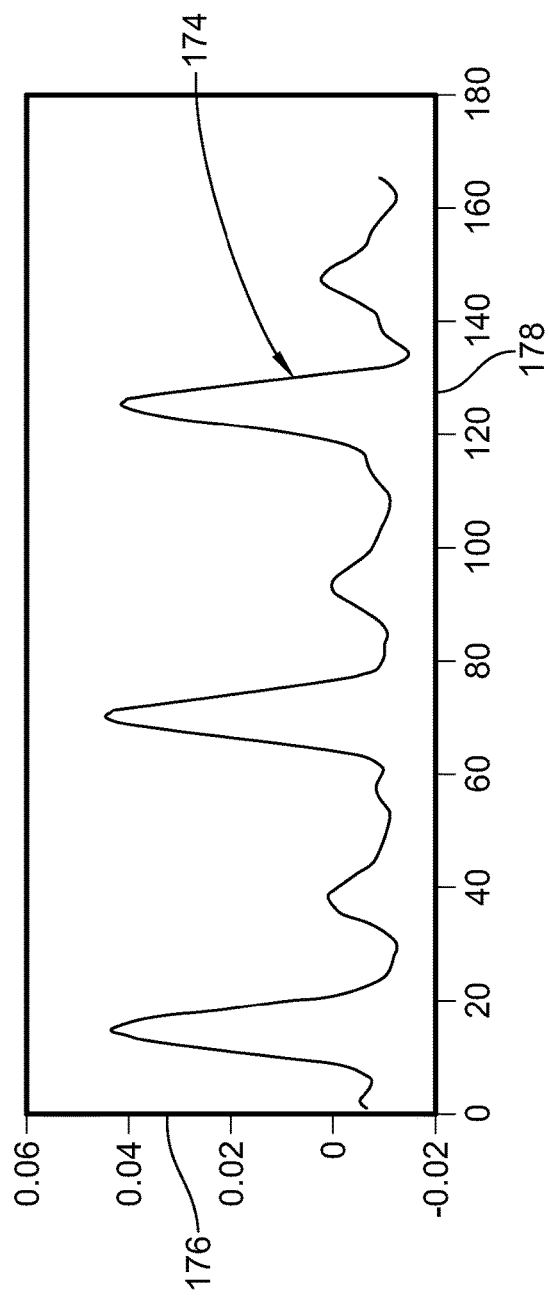
FIG. 7

RESPIRATION RATE ESTIMATION FROM A PHOTOPLETHYSMOGRAPHY SIGNAL

CROSS-REFERENCE TO RELATED APPLICATIONS

This application claims priority under 35 U.S.C. § 119(e) to U.S. Provisional Application No. 62/574,322, filed Oct. 19, 2017, which is expressly incorporated by reference herein.

BACKGROUND

The present disclosure relates to respiratory devices and particularly, to respiratory devices that use a photoplethysmograph signal to determine a respiratory rate of a patient.

Respiratory devices that provide positive pressure to a person's airway are known. For example, there are Continuous Positive Airway Pressure (CPAP) devices that apply positive pressure to a person's airway at a substantially constant level during the person's inhalation and exhalation. There are also Bi-Level CPAP devices that apply varying levels of positive pressure to a person, such as applying a first amount of positive pressure during inhalation and a second amount of positive pressure during exhalation.

Respiratory devices that provide negative pressure or suction to a person's airway are also known. One category of such devices is mechanical insufflation/exsufflation (MIE) devices. These devices are sometimes referred to as cough assist devices. This is because application of positive pressure followed by application of negative pressure to a person's airway simulates a cough and assists the person in expelling mucus from their airway. One such known cough assist device is the VITALCOUGH™ System available from Hill-Rom Company, Inc. In this regard, see U.S. Pat. No. 8,539,952 which is hereby incorporated by reference herein.

Respiratory devices that are capable of applying both positive and negative pressure to a person's airway sometimes have a pressure source, such as a blower, and at least one valve that changes position to selectively connect either the outlet of the blower or the inlet of the blower to a patient interface, such as a mask or mouthpiece and related tubing, to apply the positive pressure or the negative pressure, respectively to the person's airway. Other respiratory devices have separate positive pressure and negative pressure sources.

Some respiratory devices include additional structural elements, such as one or more valves, diaphragm pumps, acoustic devices, or piezoelectric devices that operate to provide oscillations in the baseline pressure levels being applied to the person's airway. These additional structural elements to produce the oscillations add cost, size and weight to the respiratory device. Patients and caregivers, therefore, may appreciate respiratory devices capable of producing oscillatory pressures, such as positive pressures or negative pressures or both, but that are smaller, less expensive, and lighter in weight than known respiratory devices.

It is desirable in some respiratory devices to measure respiration rate. It also desirable to measure respiration rate without the need of additional equipment that would not otherwise be in use with the patient. That is, it is desirable to measure respiration rate using existing equipment in the patient room. Thus, there is an ongoing need for improvements in the respiration rate measurement techniques of respiratory devices.

SUMMARY

The present disclosure includes one or more of the features recited in the appended claims and/or the following features which, alone or in any combination, may comprise patentable subject matter.

According to one aspect of the embodiments, a method of determining respiratory rate from a photoplethysmograph signal may include filtering the photoplethysmograph signal to create a filtered photoplethysmograph signal. The method may also include detecting peaks and valleys in the filtered photoplethysmograph signal to extract predetermined features from the filtered photoplethysmograph signal. The method may also include obtaining variation waveforms from the predetermined features. The method may also include removing outliers from each of variation waveforms. The method may also include interpolating for the outliers removed from each of the variation waveforms to acquire a frequency estimation of each of the variation waveforms. The method may also include determining a respiratory rate based on the frequency estimation of each of the variation waveforms. The method may also include determining a weighted average of the respiratory rate the variation waveforms to determine an estimated respiratory rate.

In some embodiments, the method may require determining a seven point moving average of the estimated respiratory rate. The method may require moving data of the photoplethysmograph signal by one second and repeating the steps.

Alternatively or additionally, filtering the photoplethysmograph signal may require filtering the photoplethysmograph signal with a 0.5-8 Hertz band pass filter. In some embodiments, filtering the photoplethysmograph signal may require filtering the photoplethysmograph signal with a finite impulse response filter. Filtering the photoplethysmograph signal may require filtering the photoplethysmograph signal with a filter order of 128. Filtering the photoplethysmograph signal may require filtering the photoplethysmograph signal to remove a direct current component of the photoplethysmograph signal and unwanted noise outside of a predetermined frequency range.

If desired, detecting peaks and valleys in the filtered photoplethysmograph signal may require acquiring a window of data in the photoplethysmograph signal. Detecting peaks and valleys in the filtered photoplethysmograph signal may require determining a derivative of the photoplethysmograph signal within the window of data. Detecting peaks and valleys in the filtered photoplethysmograph signal may require determining data points greater than a maximum of the derivative. Detecting peaks and valleys in the filtered photoplethysmograph signal may require detecting zero crossings of the data points by moving the window of data forward to determine the peaks of the photoplethysmograph signal. Detecting peaks and valleys in the filtered photoplethysmograph signal may require detecting zero crossings of the data points by moving the window of data backwards to determine the valleys of the photoplethysmograph signal.

Optionally, obtaining variation waveforms may require obtaining a respiration induced frequency variation (RIFV) waveform, a respiration induced intensity variation (RIIV) waveform, and a respiration induced amplitude variation (RIAV) waveform.

It is contemplated that, removing outliers from each of variation waveforms may require computing a mean and standard deviation of each of the variation waveforms. Removing outliers from each of variation waveforms may require removing outliers within ±1.5 standard deviations. Interpolating for the outliers removed from each of the variation waveforms may require linearly interpolating over the outliers.

In some embodiments, the method requires automatically adjusting a respirator based on the estimated respiratory rate.

According to another aspect of the embodiments, a respiratory system may include a respirator having a controller. A pulse oximeter may be electrically coupled to the respirator. The pulse oximeter may measure a photoplethysmograph signal. The controller may determine a respiratory rate from the photoplethysmograph signal by filtering the photoplethysmograph signal to create a filtered photoplethysmograph signal. The controller may further determine a respiratory rate from the photoplethysmograph signal by detecting peaks and valleys in the filtered photoplethysmograph signal to extract predetermined features from the filtered photoplethysmograph signal. The controller may further determine a respiratory rate from the photoplethysmograph signal by obtaining variation waveforms from the predetermined features. The controller may further determine a respiratory rate from the photoplethysmograph signal by removing outliers from each of variation waveforms. The controller may further determine a respiratory rate from the photoplethysmograph signal by interpolating for the outliers removed from each of the variation waveforms to acquire a frequency estimation of each of the variation waveforms. The controller may further determine a respiratory rate from the photoplethysmograph signal by determining a respiratory rate based on the frequency estimation of each of the variation waveforms. The controller may further determine a respiratory rate from the photoplethysmograph signal by determining a weighted average of the respiratory rate the variation waveforms to determine an estimated respiratory rate.

Optionally, the controller determines a seven point moving average of the estimated respiratory rate. The controller may move data of the photoplethysmograph signal by one second and repeats the steps.

Alternatively or additionally, the controller may filter the photoplethysmograph signal with a 0.5-8 Hertz band pass filter. The controller may filter the photoplethysmograph signal with a finite impulse response filter. The controller may filter the photoplethysmograph signal with a filter order of 128. The controller may filter the photoplethysmograph signal to remove a direct current component of the photoplethysmograph signal and unwanted noise outside of a predetermined frequency range.

It is contemplated that, the controller may detect peaks and valleys in the filtered photoplethysmograph by acquiring a window of data in the photoplethysmograph signal. The controller may detect peaks and valleys in the filtered photoplethysmograph by determining a derivative of the photoplethysmograph signal within the window of data. The controller may detect peaks and valleys in the filtered photoplethysmograph by determining data points greater than a maximum of the derivative. The controller may detect peaks and valleys in the filtered photoplethysmograph by detecting zero crossings of the data points by moving the window of data forward to determine the peaks of the photoplethysmograph signal. The controller may detect peaks and valleys in the filtered photoplethysmograph by detecting zero crossings of the data points by moving the window of data backwards to determine the valleys of the photoplethysmograph signal.

In some embodiments, the variation waveforms obtained may include a respiration induced frequency variation (RIFV) waveform, a respiration induced intensity variation (RIIV) waveform, and a respiration induced amplitude variation (RIAV) waveform.

If desired, the controller may remove outliers from each of variation waveforms by computing a mean and standard deviation of each of the variation waveforms. The controller may remove outliers from each of variation waveforms by removing outliers within ±1.5 standard deviations. The controller may interpolate for the outliers removed from each of the variation waveforms by linearly interpolating over the outliers.

In some embodiments, the controller may automatically adjust the respirator based on the estimated respiratory rate.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 4 is a graph showing the magnitude response and the phase response of the photoplethysmograph signal passed through a band pass filter;

FIG. 7 is a graph showing the filtered photoplethysmograph signal in a 2 second window and a derivative of the 2 second window of the filtered photoplethysmograph signal;

DETAILED DESCRIPTION

Figure 1:
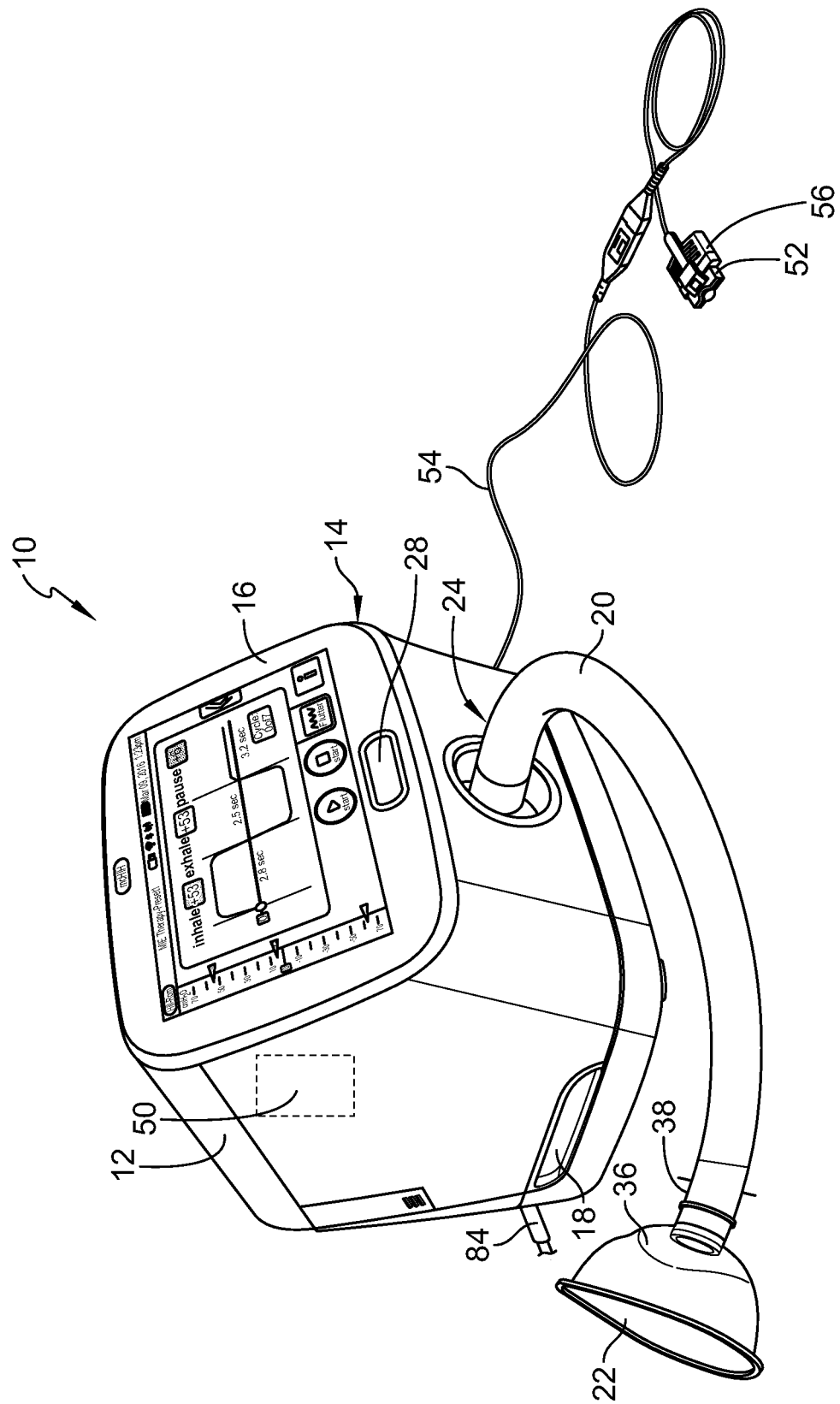
FIG. 1 is a perspective view of a respiratory device having a patient interface including a hose and a mask at an end of the hose and a pulse oximeter to measure a patients respiratory rate.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A respiratory device 10 includes a housing 12 having a front wall 14 on which a display or graphical user interface 16 is accessible to enter user inputs into device 10 and to view displayed information regarding the operation of device 10 as shown in FIG. 1. Each side of housing 12 is configured with a handle 18 near its bottom which is gripped by a person to carry device 10. At a bottom region of front wall 14 of housing 12, a hose 20 of a patient interface 22 is attached to a hose port 24. Beneath the graphical user interface 16 there is an on/off button 28 that is pressed sequentially to turn device 10 on and off. Additional details of a suitable respiratory device may be found in International Application No. PCT/SG2016/050166, filed Apr. 1, 2016, published as WO 2016/159889 A1 on Oct. 6, 2016, and titled "Manifold for Respiratory Device," which is hereby incorporated by reference herein in its entirety.

Device 10 is operable as an insufflation/exsufflation device or, as such devices are sometimes called, a cough assist device. Thus, device 10 is capable of applying positive pressure and negative pressure to a patient's airway, the positive pressure being applied during insufflation and the negative pressure being applied during exsufflation. The device 10 may be controlled to apply the positive insufflation pressure or the negative insufflation pressure to the patient through the patient interface 22. The user may operate the device 10 manually to switch between insufflation, exsufflation, and pause pressures. Device 10 also has an automatic mode in which insufflation, exsufflation, and pause pressures are controlled by the circuitry of device 10. In some embodiments, device 10 is operable to provide other modes of respiratory therapy such as continuous positive expiratory pressure (CPEP) and continuous high frequency oscillation (CHFO), just to name a couple. CPEP and CHFO are sometimes referred to herein, collectively, as Intrapulmonary Percussive Ventilation (IPV).

In the illustrative example, patient interface 22 includes a mask 36 which is configured to engage a patient's face and generally seal the area around the patient's nose and mouth. In other embodiments, patient interface 22 includes a mouthpiece rather than the illustrative mask 36 and the mouthpiece has an end portion that a patient places inside his or her mouth. Patient interface 22 includes a first tubular segment 38 extending from mask 36 and coupled to the hose 20.

The device 10 includes a controller 50 (illustrated diagrammatically in dashed lines in FIG. 1) positioned within the housing 12. The controller 50 may be embodied as a microcontroller, microprocessor, digital signal processor, system-on-chip or any other electronic component capable of controlling the operation of the device 10. The controller 50 may include components typical of an electronic microcontroller, for example memory and a central processing unit.

A pulse oximeter 52 is electrically coupled to the device 10 via a cable 54. In some embodiments, the cable 54 includes a universal serial bus (USB) connector that is configured to connect to a USB port (not shown) provided on the housing 12. The pulse oximeter 52 provides a non-invasive method for monitoring a patient's oxygen saturation ($SO_2$) through a finger monitor 56 that is positioned on the patient's finger. In some embodiments, the pulse oximeter provides data related to the patient's peripheral oxygen saturation ($SpO_2$). In other embodiments, a monitor may be provided to measure the patient's arterial oxygen saturation ($SaO_2$) from arterial blood gas analysis. In some embodiments, the pulse oximeter 52 may be coupled to the patient's earlobe, foot, or any other thin part of the patient's body. The pulse oximeter 52 passes two wavelengths of light through the body part to a photodetector. The pulse oximeter 52 measures the changing absorbance at each of the wavelengths, allowing the pulse oximeter 52 to determine absorbency due to the pulsing arterial blood alone, excluding venous blood, skin, bone, muscle, and fat.

The pulse oximeter 52 is operable to detect data related to the patient's $SpO_2$ and heart rate. The pulse oximeter 52 also detects a photoplethysmograph signal (PPG) of the patient. The data acquired by the pulse oximeter 52 is transmitted to the device 10. The device 10 may display the data on the graphical user interface 16. As described in more detail below, the controller 50 is also operable to use the data to determine variation waveforms related to the patient's respiratory rate. While it may be known to acquire variation waveforms from raw PPG data, the methods described herein provide unique steps and data manipulation that are not currently applied to raw PPG data. As a result, the methods described herein represent an improvement over known methods for acquiring variation waveforms.

Figure 2:
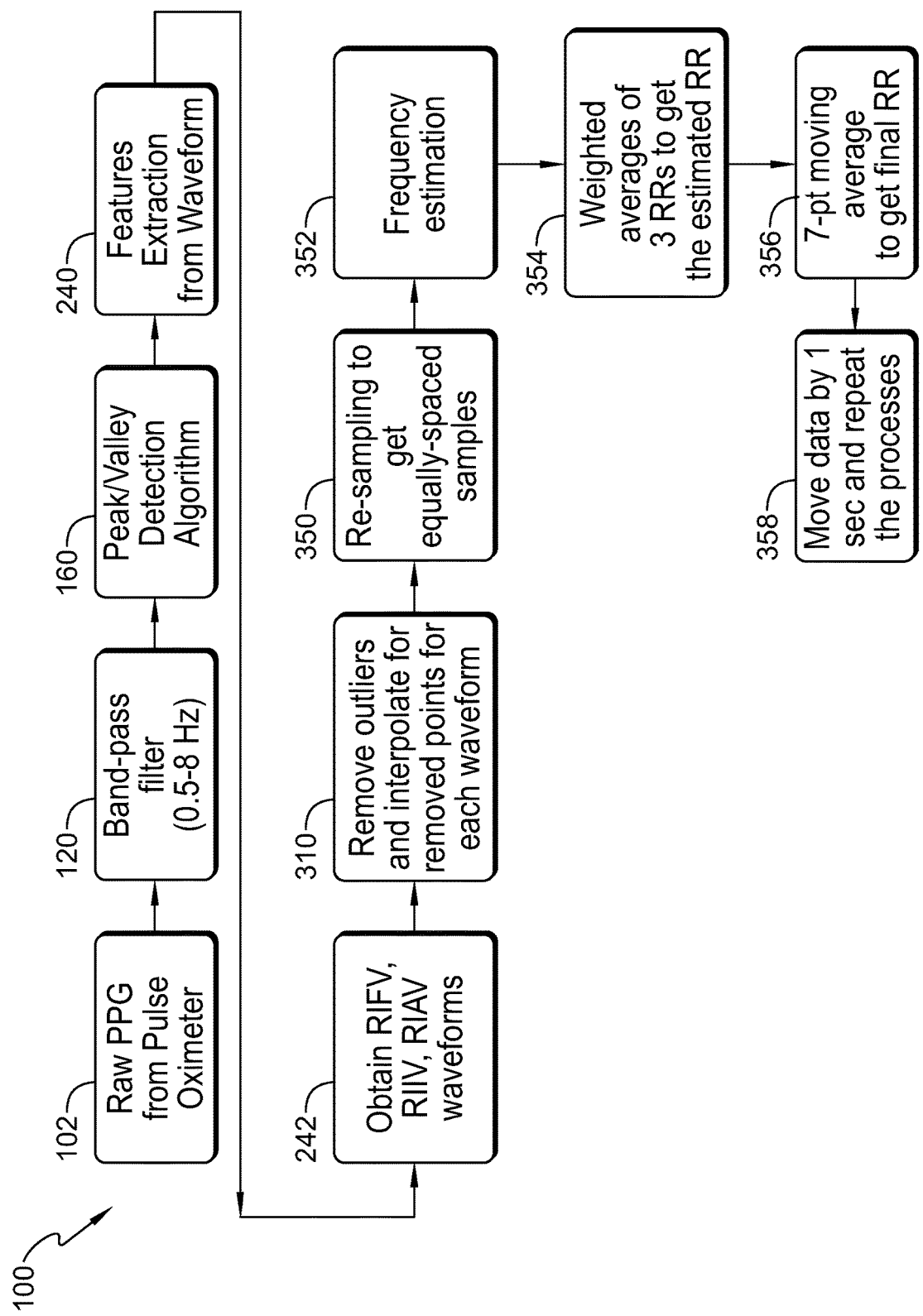
FIG. 2 is a block diagram showing a method for determining a respiratory rate based on an acquired photoplethysmograph signal.
Figure 3:
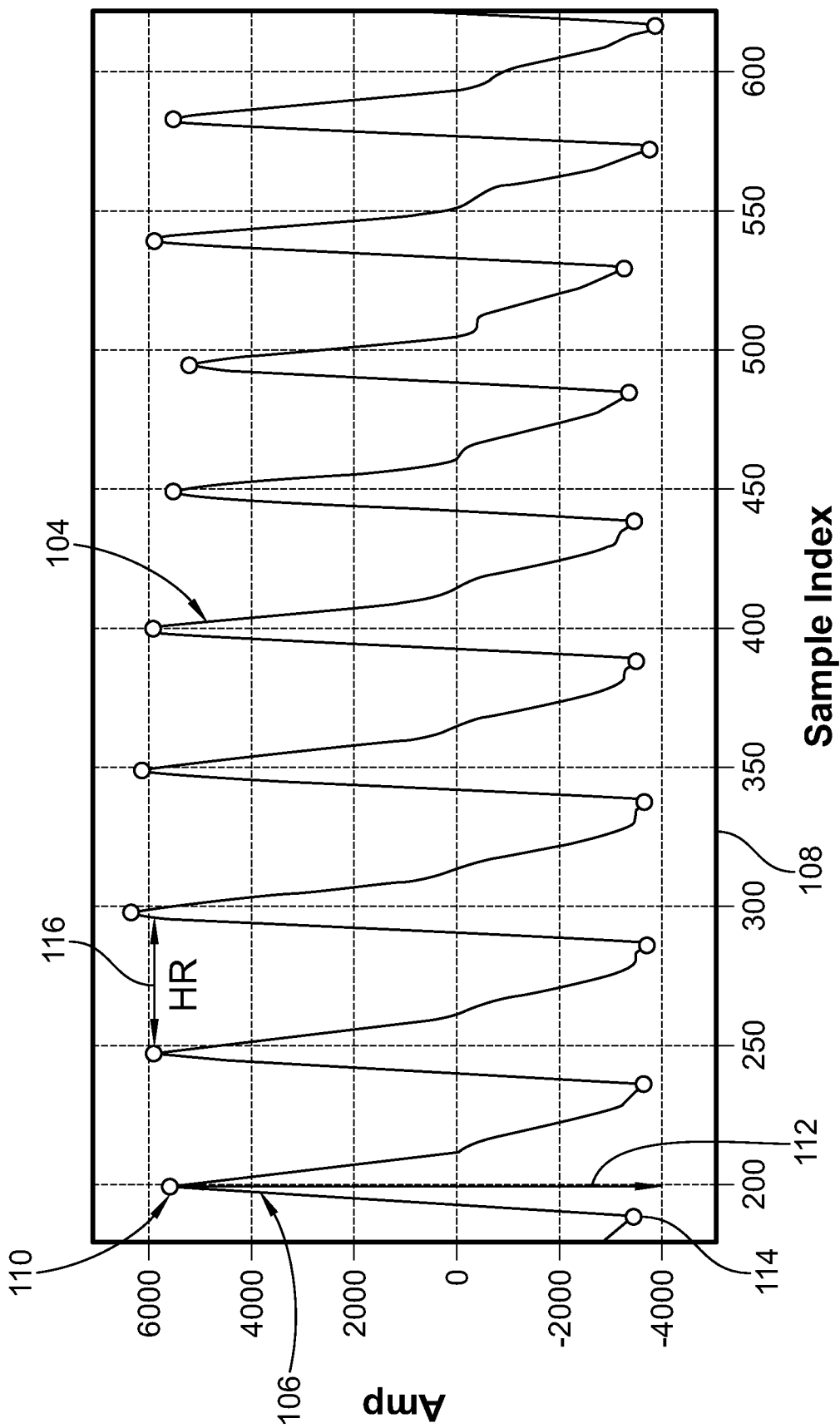
FIG. 3 is a graph showing an example of a raw photoplethysmograph signal acquired by the pulse oximeter.

According to the method 100 of FIG. 2, the controller 50 acquires a raw PPG signal from pulse oximeter 52 at step 102 and processes the data to determine a respiratory rate of the patient. Referring to FIG. 3, the raw PPG signal 104 can be graphed as amplitude, between 0-65535 analog to digital converter (ADC) values (y-axis) 106 over a sample index (x-axis) 108. From the raw PPG signal 104, a maximum intensity 110 of the PPG signal 104 is found at a peak amplitude of the PPG signal 104. The maximum intensity 110 indicates the intensity of light which reflects the absorption of light from the blood. Additionally, an amplitude 112 of the PPG signal 104 is taken as the difference between the maximum intensity 110 and the minimum intensity 114. Moreover, the heart rate 116 of the patient is a function of the number of samples between each maximum intensity 110. The maximum intensity 110, the amplitude 112 and the heart rate 116 may be processed by the controller 50 to determine a respiration induced frequency variation (RIFV) waveform, a respiration induced intensity variation (RIIV) waveform, and a respiration induced amplitude variation (RIAV) waveform, which are discussed in further detail below.

Figure 5:
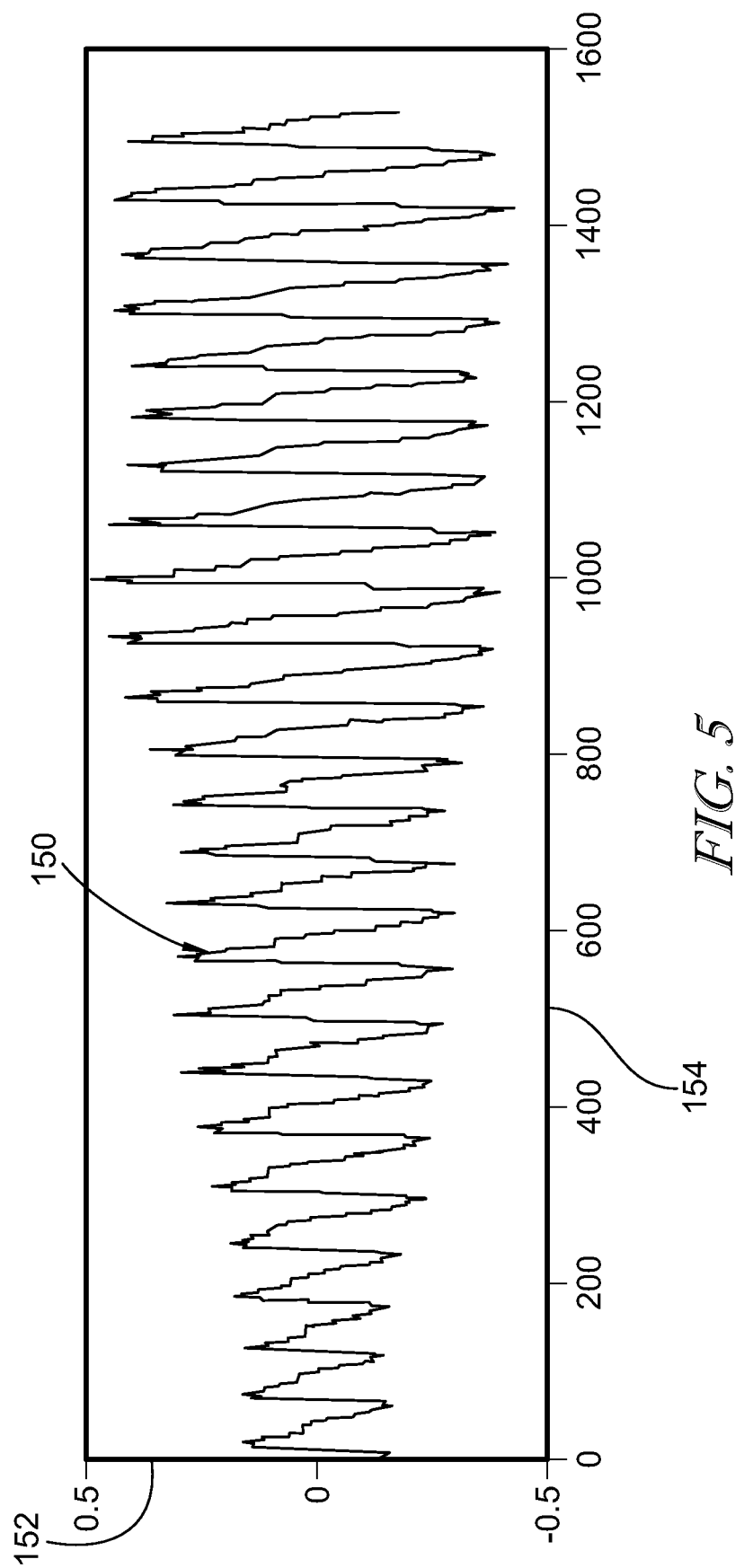
FIG. 5 is a graph showing a filtered photoplethysmograph signal.

Referring back to FIG. 2, a band pass filter is applied to the raw PPG signal 104, at step 120. The band pass filter is a finite impulse response filter (FIR filter) in some embodiments; however, other filters may be applied. In some embodiments, the band pass filter has a frequency range of 0.5-8 Hz to remove a direct current component and unwanted noise which falls outside the frequency range of interest in the raw PPG signal. In some embodiments, other band pass filter frequency ranges may be applied. In an illustrative embodiment, a band pass filter having a filter order of 128 is applied to the raw PPG signal. In some embodiments, the band pass filter may have another filter order. An illustrative frequency response of the band pass filter is shown in FIG. 4. A magnitude response 122 of the band pass filter is shown in graph 124 as a function of magnitude (in decibels) (y-axis) 126 over a normalized frequency of (π*radian)/sample (x-axis) 128. The magnitude response 122 has an attenuation of about 100 decibels. An illustrative phase response 130 of the band pass filter is shown in graph 132 as a function of phase (in degrees) (y-axis) 134 over a normalized frequency of (π*radian)/sample (x-axis) 136. The phase response 130 has an attenuation of about 2100 degrees. An illustrative filtered PPG signal 150 is shown in FIG. 5 as a function of amplitude (y-axis) 152 over sample index (x-axis) 154. The filtered PPG signal 150 has an amplitude between −0.5 and 0.5 ADC values.

Figure 6:
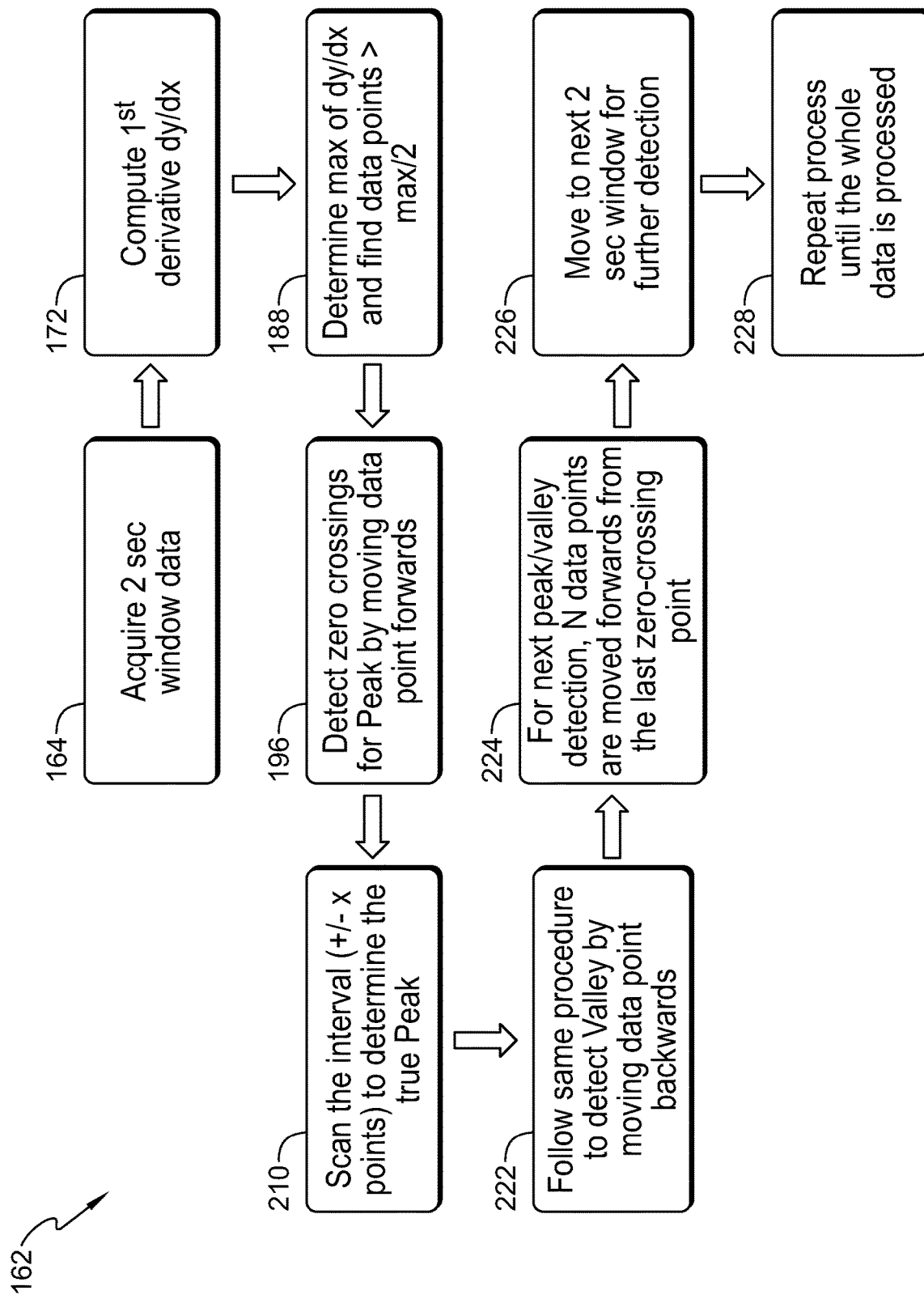
FIG. 6 is a block diagram of a method of determining peaks and valleys in the filtered photoplethysmograph signal.

Referring back to FIG. 2 the controller 50 performs peak and valley detection on the filtered PPG signal 150, at step 160. A method 162 of peak and valley detection is illustrated in FIG. 6. Initially, the controller 50 acquires a 2 second window of data from the filtered PPG signal 150, at step 164. An illustrative 2 second sample of data 166 is shown in the upper graph of FIG. 7 as a function of normalized amplitude (y-axis) 168 over sample index (x-axis) 170. The 2 second sample data 166 is illustrated as being taken over the first 180 samples of the sample index 170; however, any 2 second window of data may be applied. The illustrative sample data 166 has an amplitude 168 between approximately −0.2 and 0.2 ADC values. It should be recognized that the amplitude 168 of the sample data 166 is patient specific. The sample data 166 is shown with three peaks with graduated slope between each peak. Referring back to FIG. 6, a first derivative of the sample data 166 is taken, at step 172, to smooth the sample data 166. The first derivative 174 is illustrated in the lower graph of FIG. 7 as a function of amplitude (y-axis) 176 over sample index (x-axis) 178. It should be appreciated that the sample index 178 remains between 0 and 180. The amplitude 176 of the first derivative 174 is between −0.02 and 0.05 ADC values. Notably, the gradual slope between peaks is replaced with smooth curves.

Figure 8:
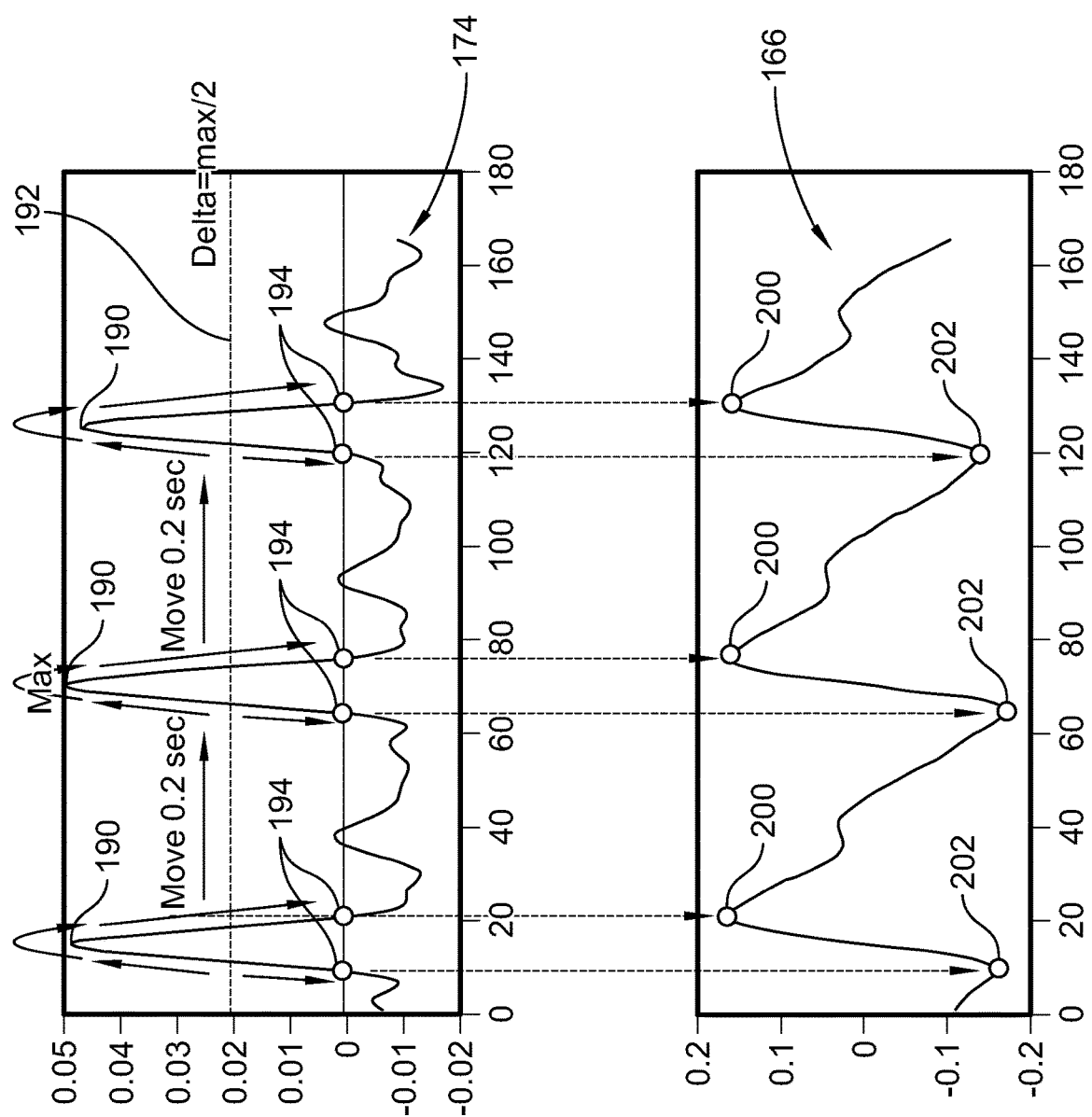
FIG. 8 is a graph showing zero crossing points in the upper graph that correspond to peaks and valleys of the photoplethysmograph signal in the lower graph.
Figure 9:
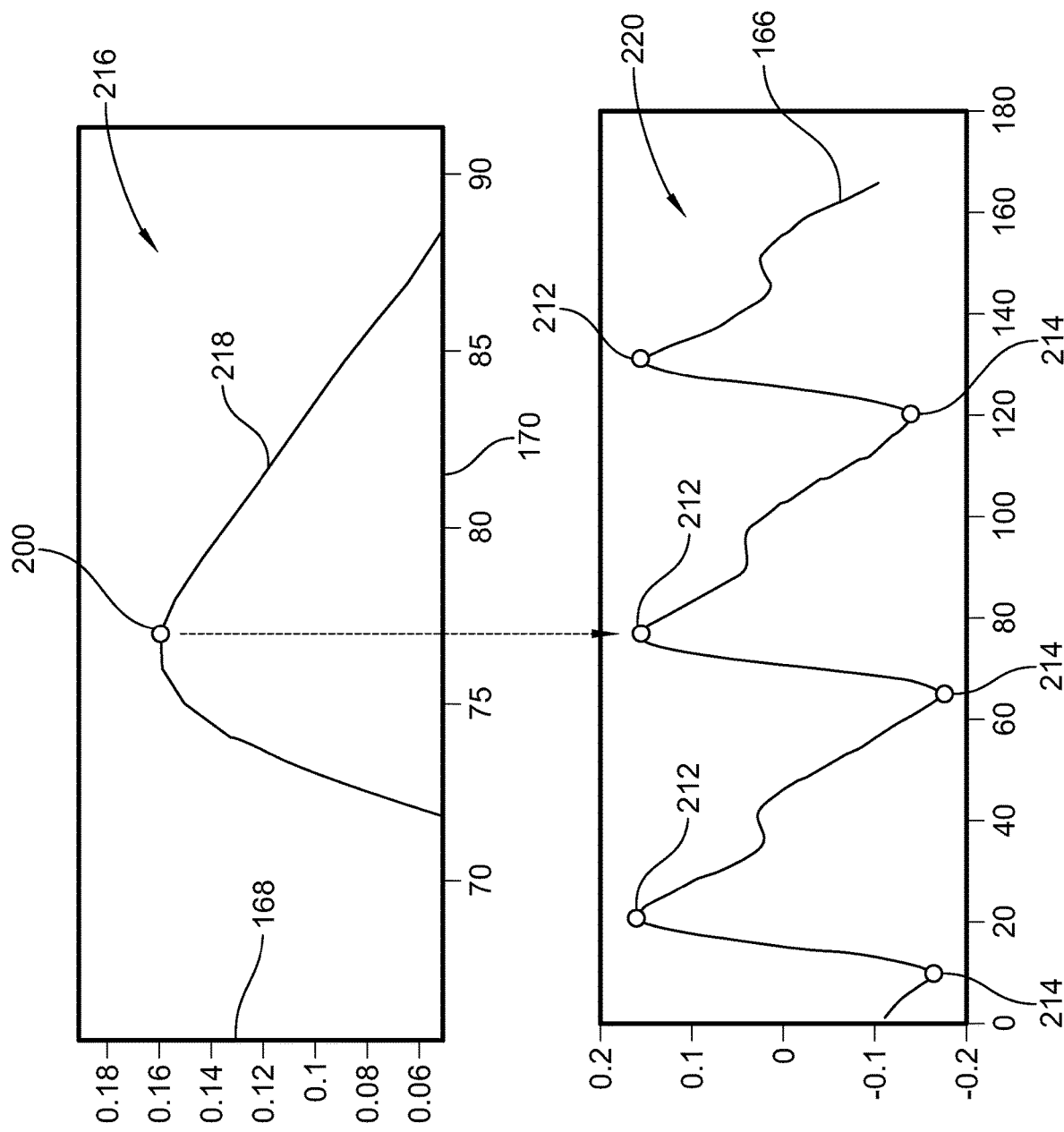
FIG. 9 is a pair of graphs showing the true peaks and valleys of the photoplethysmograph signal with the upper graph being an enlarged image portion of the lower graph.
Figure 10:
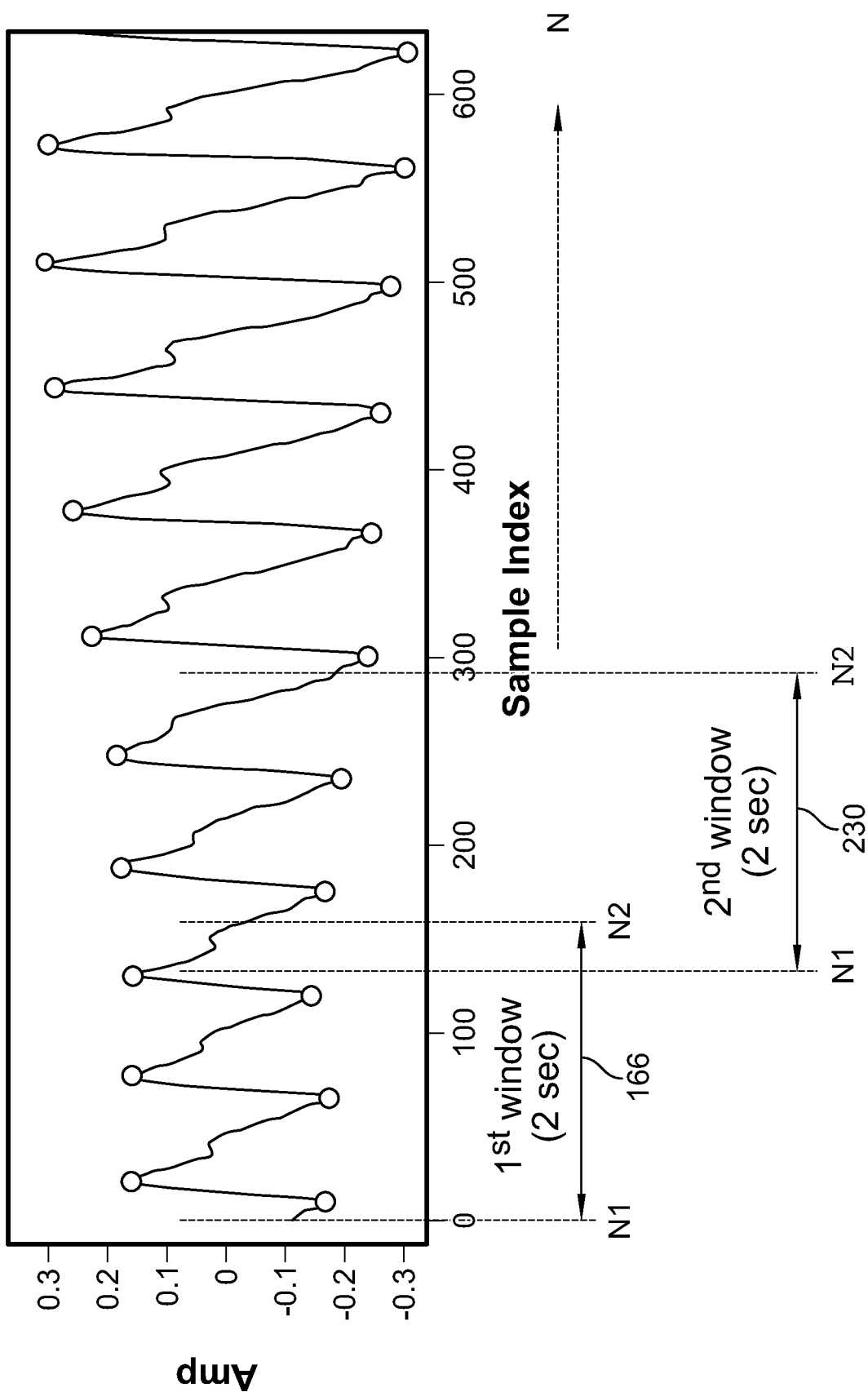
FIG. 10 is a graph showing sample index windows of the photoplethysmograph signal after filtration and peak and valley detection.

Referring back to FIG. 6, a maximum of the first derivative 174 and data points at the maximum/2 are detected by the controller 50, at step 188. The upper graph of FIG. 8 shows the first derivative 174 with the maximums 190 and the zero axis 192 labeled. Zero crossings 194 are detected along the zero axis 192, at step 196 in FIG. 6. The points corresponding to the zero crossings 194 in the upper graph of FIG. 8 are illustrated in the lower graph of FIG. 8. The peaks 200 and valleys 202 that correlate with the zero crossings 194 of the first derivative 174 are then determined for the sample data 166. The peaks 200 and valleys 202 are illustrated in the lower graph of FIG. 8. Referring back to FIG. 6, the sample data 166 is scanned, at step 210, to determine true peaks 212 and valleys 214 in the sample data 166. The upper graph 216 of FIG. 9 illustrates a segment 218 of the sample data 166 containing the peak 200. The segment 218 is scanned by moving forward and backward along the sample index 170 until the true peak 212, illustrated in graph 220 (i.e. the lower graph of FIG. 9) is detected by changes in the amplitude 168. In some embodiments, the segment 218 is scanned by moving forward and backward 10 data points, i.e. the scan is a ±10 data point scan. Referring back to FIG. 6, step 210 is repeated, at step 222, to find the true valley 214 in the sample data 166. At step 224, the data points are moved forward to the next zero-crossing 194 to detect the next set of true peaks 212 and true valleys 214. The controller 50 then moves to a new 2 second window 230, at step 226. First and second windows are shown, for example, in the graph of FIG. 10. At step 228 of FIG. 6, steps 172, 188, 196, 210, 222, and 224 are repeated for the new 2 second window.

Referring once again to FIG. 2, the controller 50 extracts features from the filtered PPG signal 150, at step 240. As discussed above, these features include a maximum intensity of the filtered PPG signal 150, the amplitude of the filtered PPG signal 150, and the heart rate. The maximum intensity, the amplitude, and the heart rate are processed by the controller 50 to determine, at step 242 the respiration induced frequency variation (RIFV) waveform 250 (illustrated in the upper graph of FIG. 11), the respiration induced intensity variation (RIIV) waveform 270 (illustrated in the upper graph of FIG. 12), and the respiration induced amplitude variation (RIAV) waveform 290 (illustrated in the upper graph of FIG. 13). Particularly, the autonomic response to respiration causes the variation of heart rate to synchronize with the respiratory cycle. This process can be known as respiratory sinus arrhythmia (RSA) in which the heart rate increases during inspiration and decreases during expiration to provide the RIFV waveform 250. The RIIV waveform 270 is due to the variation of perfusion baseline. The RIAV waveform 290 is due to a decrease in cardiac output which is caused by reduced ventricular filling. Therefore a change in peripheral pulse strength occurs, which causes a variation of amplitudes of each PPG pulse.

Figure 11:
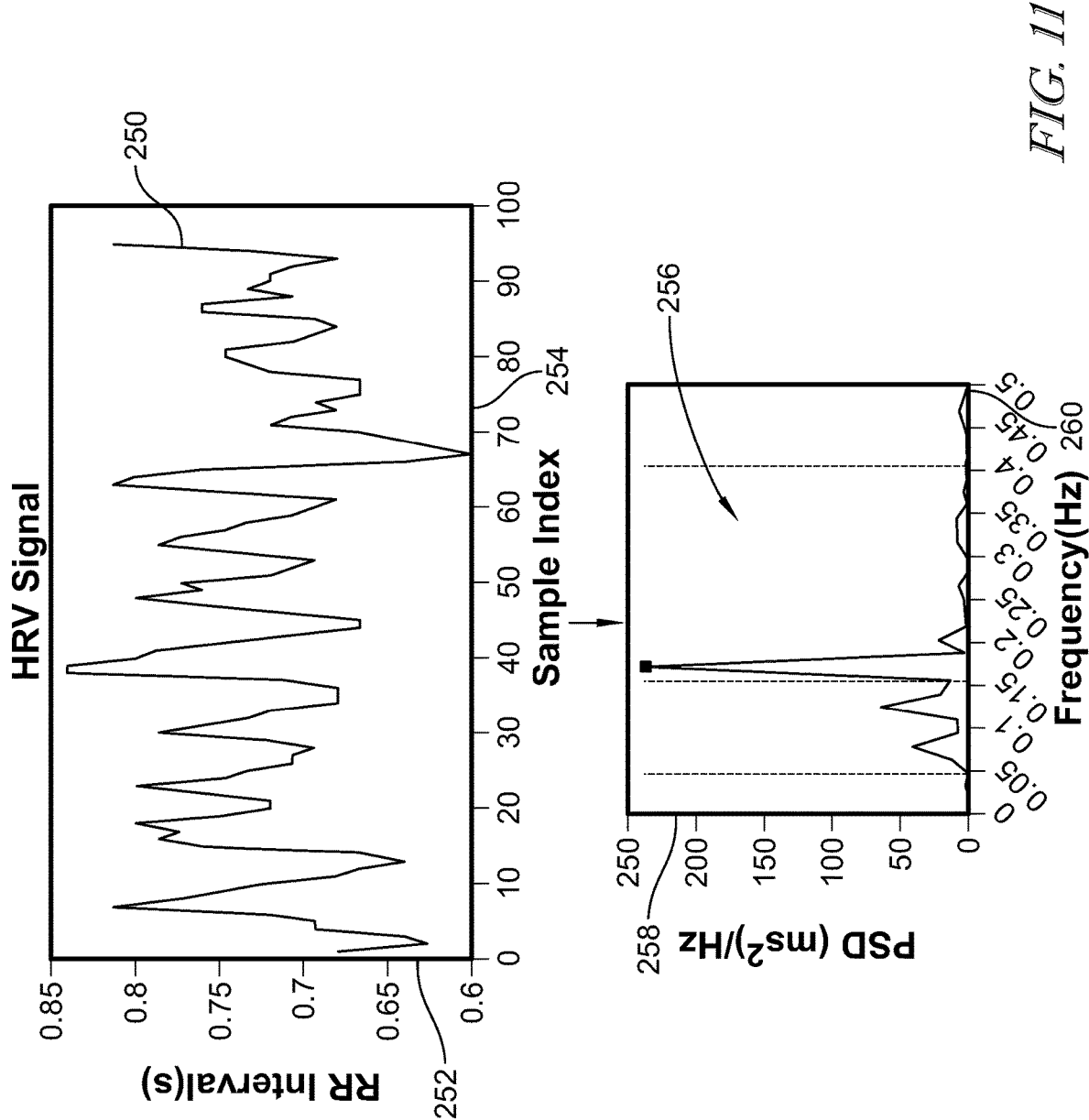
FIG. 11 is a pair of graphs showing a Respiration Induced Frequency Variation (RIFV) waveform acquired from the photoplethysmograph signal in the upper graph and a Fast Fourier Transform of the Respiration Induced Frequency Variation (RIFV) waveform in the lower graph.
Figure 12:
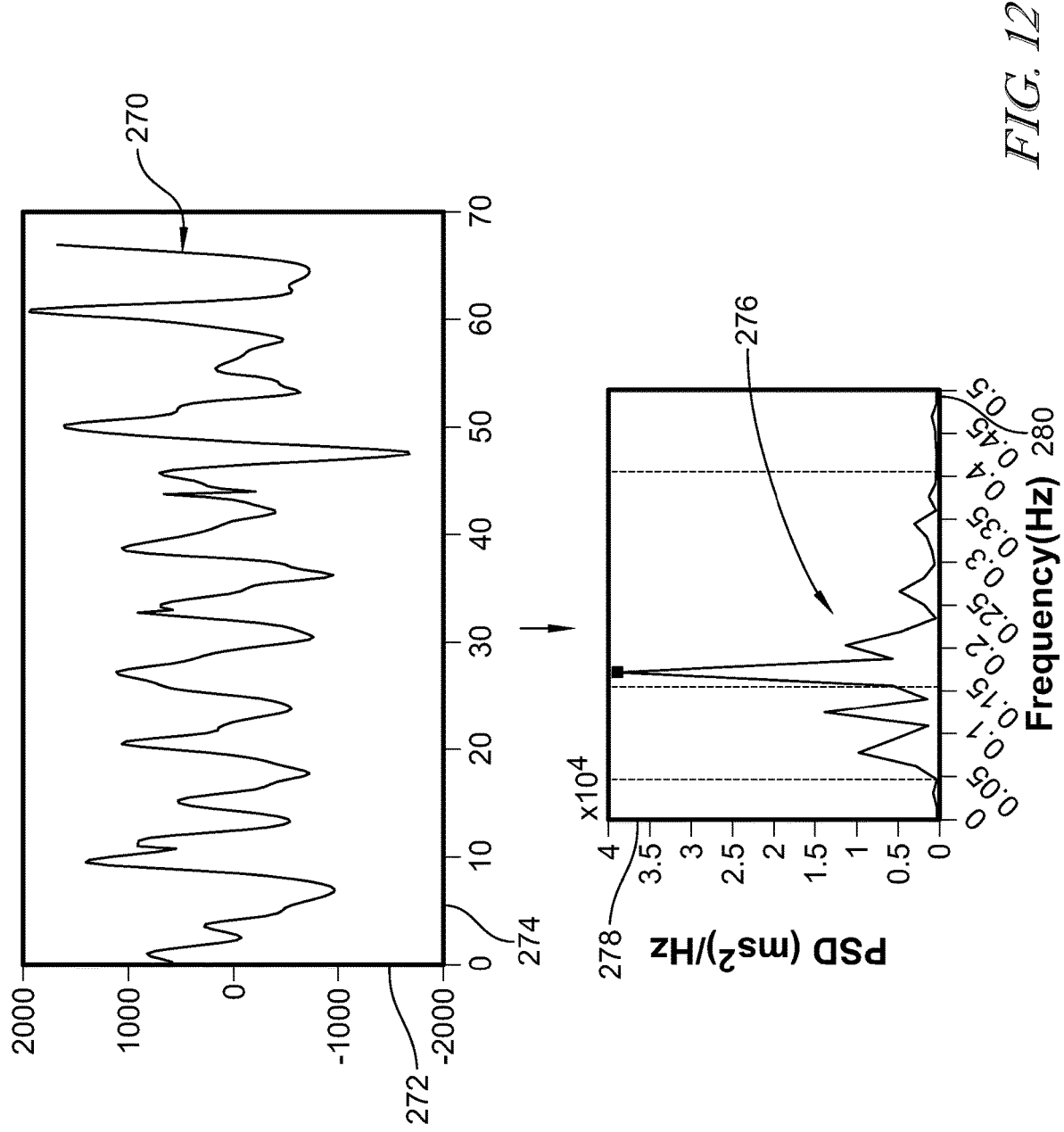
FIG. 12 is a pair of graphs showing a Respiration Induced Intensity Variation (RIIV) waveform acquired from the photoplethysmograph signal in the upper graph and a Fast Fourier Transform of the Respiration Induced Intensity Variation (RIIV) waveform in the lower graph.
Figure 13:
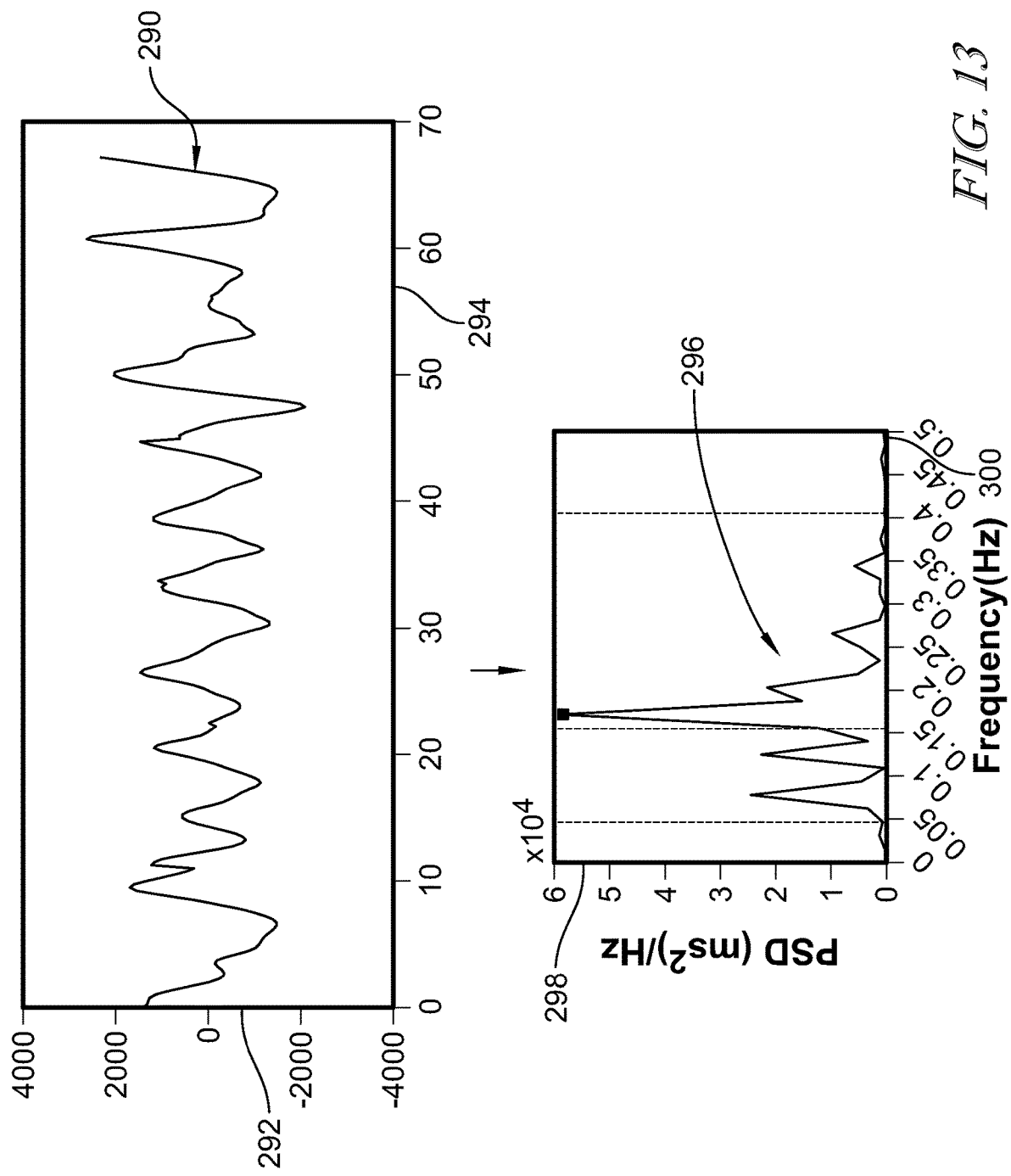
FIG. 13 illustrates is a pair of graphs showing a Respiration Induced Amplitude Variation (RIAV) waveform acquired from the photoplethysmograph signal in the upper graph and a Fast Fourier Transform of the Respiration Induced Amplitude Variation (RIAV) waveform in the lower graph.

Referring to FIG. 11, the RIFV waveform 250, shown in the upper graph, is measured as a function of the respiratory rate in seconds (y-axis) 252 over the sample index (x-axis) 254. In the illustrative embodiment, the respiratory rate 252 is between 0.6 seconds and 0.85 seconds. A Fast Fourier Transform 256 of the RIFV waveform 250 provides the proportional summation difference 258 of the RIFV waveform 250 as a function of frequency 260, as shown in the lower graph of FIG. 11. As illustrated in the lower graph of FIG. 11, the peak frequency of the RFIV waveform 250 is between 0.15 Hz and 0.2 Hz and has a proportional summation difference of approximately 250 ms$^2$/Hz. Referring to FIG. 12, the RIIV waveform 270 shown in the upper graph is measured as a function of the intensity in ADC values (y-axis) 272 over the sample index (x-axis) 274. In the illustrative embodiment, the intensity 272 is between −2000 and 2000. A Fast Fourier Transform 276 of the RIIV waveform 270 provides the proportional summation difference 278 of the RIIV waveform 270 as a function of frequency 280, as shown in the lower graph of FIG. 12. As illustrated in the lower graph of FIG. 12, the peak frequency of the RFIV waveform 270 is between 0.15 Hz and 0.2 Hz and has a proportional summation difference of approximately 40000 ms$^2$/Hz. Referring to FIG. 13, the RIAV waveform 290 shown in the upper graph is measured as a function of the phase in ADC values (y-axis) 292 over the sample index (x-axis) 294. In the illustrative embodiment, the phase 292 is between −2000 and 2000. A Fast Fourier Transform 296 of the RIAV waveform 290 provides the proportional summation difference 298 of the RIAV waveform 290 as a function of frequency 300, as shown in the lower graph of FIG. 13. As illustrated in the lower graph of FIG. 13, the peak frequency of the RFAV waveform 290 is between 0.15 Hz and 0.2 Hz and has a proportional summation difference of approximately 60000 ms$^2$/Hz.

Figure 14:
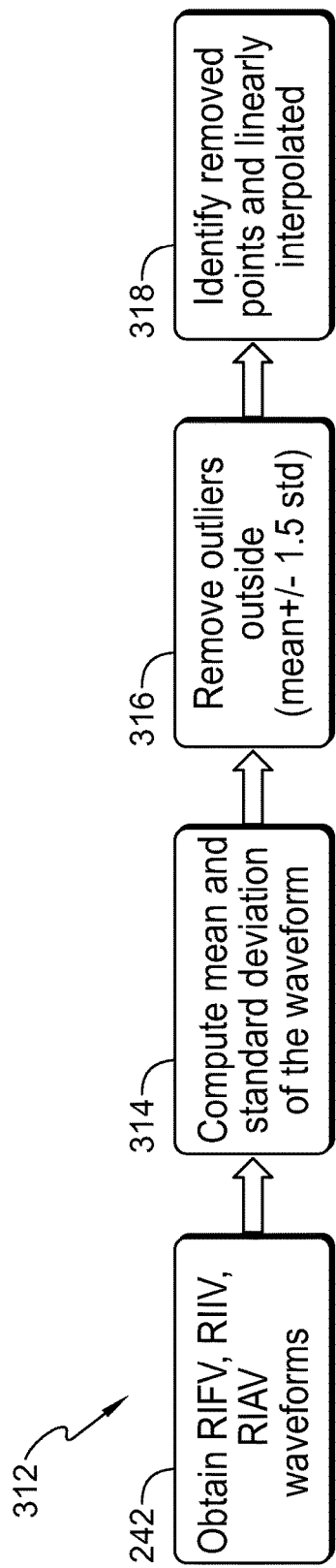
FIG. 14 is a block diagram showing a method for removing outliers from a weighted variation waveform.
Figure 15:
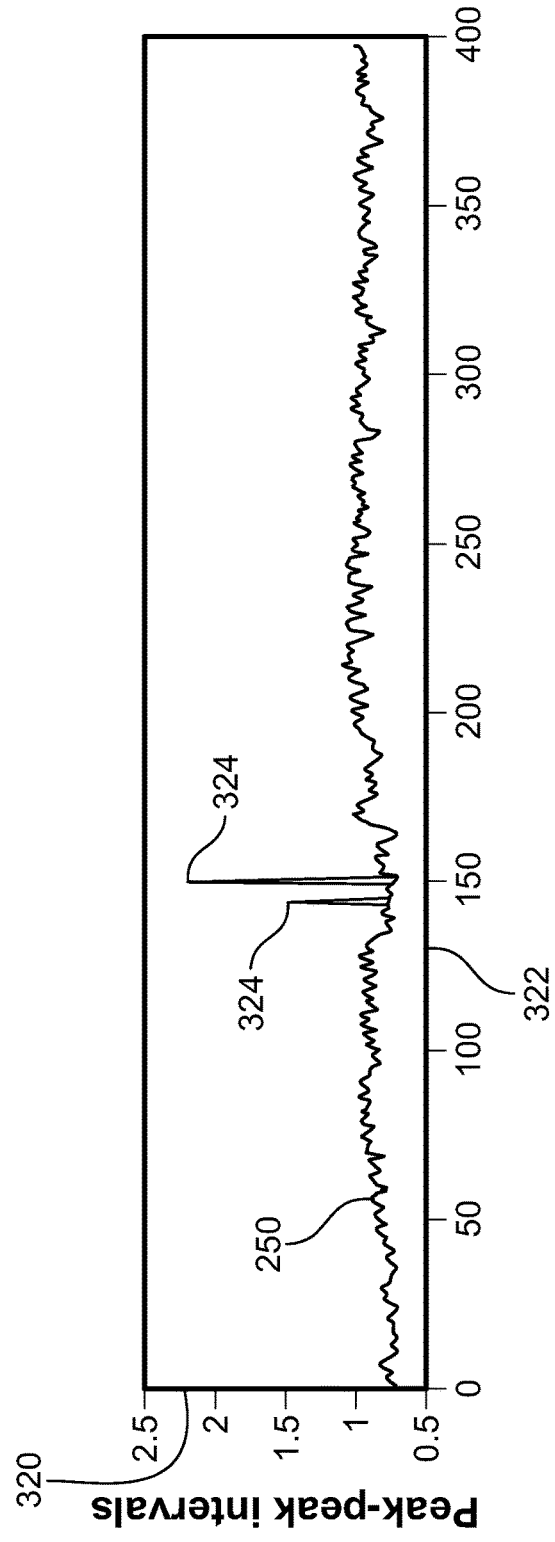
FIG. 15 is a graph showing spiked outliers that are removed from a weighted variation waveform.

Referring back to FIG. 2, outliers are removed from each of the RIFV waveform 250, RIIV waveform 270, and RIAV waveform 290 and data is interpolated into each of the RIFV waveform 250, RIIV waveform 270, and RIAV waveform 290, at step 310. FIG. 14 illustrates a method 312 for performing the step 310 that begins with the step of 242 of obtaining the RIFV waveform 250, RIIV waveform 270, and RIAV waveform 290. At step 314, the mean and standard deviation for each of the RIFV waveform 250, RIIV waveform 270, and RIAV waveform 290 is calculated. At step 316, outliers outside of the mean within a standard deviation of ±1.5 are removed from the data. FIG. 15 illustrates a RIFV waveform 250 having peak to peak intervals 320 between 0.5 and 1 along the sample index 322. Notably, 2 data points 324 are located outside of the standard deviation of ±1.5. At step 318, these points are identified and removed. The RIFV waveform 250 is then interpolated to place new data points within the standard deviation of ±1.5.

Referring back to FIG. 2, each of the RIFV waveform 250, RIIV waveform 270, and RIAV waveform 290 is resampled to obtain equally spaced samples, at step 350. A frequency estimation of each of RIFV waveform 250, RIIV waveform 270, and RIAV waveform 290 is obtained, at step 352, to determine a respiratory rate based on each of RIFV waveform 250, RIIV waveform 270, and RIAV waveform 290. The respiratory rate of the RIFV waveform 250, the respiratory rate of the RIIV waveform 270, and the respiratory rate of the RIAV waveform 290 are averaged, at step 354, to determine a weighted average of the respiratory rate. Next, a 7 point moving average of the respiratory rate is determined, at step 356 and the method 100 is repeated, at step 358, to continually monitor the patient's respiratory rate. In the illustrative example, the data is moved by 1 second and the method 100 is repeated.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A respiratory system comprising:
a respirator having a controller, and
a pulse oximeter electrically coupled to the respirator, the pulse oximeter measuring a photoplethysmograph signal,
wherein the controller determines a respiratory rate from the photoplethysmograph signal using the steps of:
(i) filtering the photoplethysmograph signal to create a filtered photoplethysmograph signal,
(ii) detecting peaks and valleys in the filtered photoplethysmograph signal to extract predetermined features from the filtered photoplethysmograph signal,
(iii) obtaining variation waveforms from the predetermined features,
(iv) removing outliers from each of the variation waveforms, wherein the controller removes outliers from each of the variation waveforms by computing a mean and standard deviation of each of the variation waveforms and removing outliers within ±1.5 standard deviations,
(v) interpolating for the outliers removed from each of the variation waveforms to acquire a frequency estimation of each of the variation waveforms, wherein the controller interpolates for the outliers removed from each of the variation waveforms by linearly interpolating over the outliers,
(vi) determining a respiratory rate based on the frequency estimation of each of the variation waveforms, and
(vii) determining a weighted average of the respiratory rate of the variation waveforms to determine an estimated respiratory rate.

2. The respiratory system of claim 1, wherein the controller determines a seven point moving average of the estimated respiratory rate.

3. The respiratory system of claim 2 wherein the controller moves data of the photoplethysmograph signal by one second and repeats steps (i)-(vii).

4. The respiratory system of claim 1, wherein the controller filters the photoplethysmograph signal with a 0.5-8 Hertz band pass filter.

5. The respiratory system of claim 4, wherein the controller filters the photoplethysmograph signal with a finite impulse response filter.

6. The respiratory system of claim 4, wherein the controller filters the photoplethysmograph signal with a filter order of 128.

7. The respiratory system of claim 4, wherein the controller filters the photoplethysmograph signal to remove a direct current component of the photoplethysmograph signal and unwanted noise outside of a predetermined frequency range.

8. The respiratory system of claim 1, wherein the controller detects peaks and valleys in the filtered photoplethysmograph by:
acquiring a window of data in the photoplethysmograph signal,
determining a derivative of the photoplethysmograph signal within the window of data,
determining data points greater than a maximum of the derivative, detecting zero crossings of the data points by moving the window of data forward to determine the peaks of the photoplethysmograph signal, and detecting zero crossings of the data points by moving the window of data backwards to determine the valleys of the photoplethysmograph signal.

9. The respiratory system of claim 1, wherein the variation waveforms obtained include a respiration induced frequency variation (RIFV) waveform, a respiration induced intensity variation (RIIV) waveform, and a respiration induced amplitude variation (RIAV) waveform.

10. The respiratory system of claim 1, wherein the controller automatically adjusts the respirator based on the estimated respiratory rate.

11. A method of determining respiratory rate from a photoplethysmograph signal, comprising the steps of:
(i) filtering the photoplethysmograph signal to create a filtered photoplethysmograph signal,
(ii) detecting peaks and valleys in the filtered photoplethysmograph signal to extract predetermined features from the filtered photoplethysmograph signal,
(iii) obtaining variation waveforms from the predetermined features,
(iv) removing outliers from each of the variation waveforms by computing a mean and standard deviation of each of the variation waveforms and removing outliers within ±1.5 standard deviations,
(v) interpolating for the outliers removed from each of the variation waveforms to acquire a frequency estimation of each of the variation waveforms by linearly interpolating over the outliers,
(vi) determining a respiratory rate based on the frequency estimation of each of the variation waveforms, and
(vii) determining a weighted average of the respiratory rate of the variation waveforms to determine an estimated respiratory rate.

12. The method of claim 11, further comprising determining a seven point moving average of the estimated respiratory rate.

13. The method of claim 12 further comprising moving data of the photoplethysmograph signal by one second and repeating steps (i)-(vii).

14. The method of claim 11, wherein filtering the photoplethysmograph signal further comprises filtering the photoplethysmograph signal with a 0.5-8 Hertz band pass filter.

15. The method of claim 14, wherein filtering the photoplethysmograph signal further comprises filtering the photoplethysmograph signal with a finite impulse response filter.

16. The method of claim 11, wherein detecting peaks and valleys in the filtered photoplethysmograph signal further comprises:
acquiring a window of data in the photoplethysmograph signal,
determining a derivative of the photoplethysmograph signal within the window of data,
determining data points greater than a maximum of the derivative,
detecting zero crossings of the data points by moving the window of data forward to determine the peaks of the photoplethysmograph signal, and
detecting zero crossings of the data points by moving the window of data backwards to determine the valleys of the photoplethysmograph signal.

17. The method of claim 11, wherein obtaining variation waveforms further comprises obtaining a respiration induced frequency variation (RIFV) waveform, a respiration induced intensity variation (RIIV) waveform, and a respiration induced amplitude variation (RIAV) waveform.

\* \* \* \* \*